(12) United States Patent
Kruspe et al.

(10) Patent No.: US 9,062,532 B2
(45) Date of Patent: Jun. 23, 2015

(54) ELECTROMAGNETIC VISCOSITY SENSOR

(75) Inventors: Thomas Kruspe, Niedersachsen (DE); Stefan Sroka, Niedersachsen (DE)

(73) Assignee: Baker Hughes Incorporated, Houston, TX (US)

( * ) Notice: Subject to any disclaimer, the term of this patent is extended or adjusted under 35 U.S.C. 154(b) by 546 days.

(21) Appl. No.: 13/412,801

(22) Filed: Mar. 6, 2012

(65) Prior Publication Data

US 2012/0227483 A1    Sep. 13, 2012

Related U.S. Application Data

(60) Provisional application No. 61/451,342, filed on Mar. 10, 2011.

(51) Int. Cl.
| | | |
|---|---|---|
| *E21B 47/00* | (2012.01) | |
| *G01N 11/16* | (2006.01) | |
| *E21B 47/09* | (2012.01) | |
| *G01N 11/00* | (2006.01) | |

(52) U.S. Cl.
CPC ......... *E21B 47/0905* (2013.01); *E21B 47/0002* (2013.01); *G01N 11/16* (2013.01); *G01N 2011/0086* (2013.01)

(58) Field of Classification Search
CPC ............... G01N 11/16; G01N 11/162; G01N 2011/0086
USPC ................. 73/504.04, 504.14–504.16, 64.53, 73/152.18
See application file for complete search history.

(56) References Cited

U.S. PATENT DOCUMENTS

| 2,696,735 | A | * | 12/1954 | Woodward | .................... | 73/54.26 |
|---|---|---|---|---|---|---|
| 2,839,915 | A | * | 6/1958 | Rich et al. | .................... | 73/54.25 |
| 2,973,639 | A | * | 3/1961 | Banks | .......... | 73/54.25 |
| 3,100,390 | A | * | 8/1963 | Banks | .......... | 73/32 A |
| 3,145,559 | A | * | 8/1964 | Banks | .......... | 73/32 A |
| 3,177,705 | A | * | 4/1965 | Banks | .......... | 73/54.25 |
| 3,270,274 | A | * | 8/1966 | Banks | .......... | 323/298 |
| 3,282,084 | A | * | 11/1966 | Banks | .......... | 73/32 A |
| 3,349,604 | A | * | 10/1967 | Banks | .......... | 73/32 A |
| 3,382,706 | A | * | 5/1968 | Fitzgerald et al. | .......... | 73/54.25 |
| 3,474,663 | A | * | 10/1969 | McLatchie et al. | .......... | 73/54.25 |
| 3,603,137 | A | * | 9/1971 | Banks | .......... | 73/32 R |
| 3,734,119 | A | * | 5/1973 | Nudds | .......... | 137/92 |
| 4,341,111 | A | * | 7/1982 | Husar | ............ | 73/64.42 |
| 4,488,427 | A | * | 12/1984 | Matusik et al. | .............. | 73/54.23 |
| 4,875,362 | A | * | 10/1989 | Skallen | ........ | 73/54.31 |
| 4,964,301 | A | * | 10/1990 | Lysen | .......... | 73/29 R |
| 5,067,344 | A | * | 11/1991 | Fitzgerald et al. | .......... | 73/54.24 |
| 5,604,441 | A | | 2/1997 | Freese, V et al. | | |

(Continued)

OTHER PUBLICATIONS

Notification of Transmittal of the International Search Report and the Written Opinion of the International Searching Authority, or the Declaration; PCT/US2012/028495; Oct. 16, 2012.

(Continued)

*Primary Examiner* — John Fitzgerald
(74) *Attorney, Agent, or Firm* — Cantor Colburn LLP

(57) ABSTRACT

An apparatus for estimating a property of a downhole fluid includes: a flexural mechanical resonator having at least one magnetic permeable element traversing a pressure-retaining wall with a portion of the magnetic permeable element protruding into the fluid, the portion of the magnetic permeable element protruding into the fluid being configured to oscillate; and a monitor for receiving a response of the flexural mechanical resonator to estimate the property.

23 Claims, 5 Drawing Sheets

(56) References Cited

U.S. PATENT DOCUMENTS

| | | |
|---|---|---|
| 6,393,895 B1 | 5/2002 | Matsiev et al. |
| 6,938,470 B2 | 9/2005 | DiFoggio et al. |
| 7,010,978 B1 | 3/2006 | Harris et al. |
| 2010/0246317 A1* | 9/2010 | Wilson .......................... 366/142 |
| 2012/0227483 A1* | 9/2012 | Kruspe et al. .............. 73/152.55 |

OTHER PUBLICATIONS

Clara, "A Viscosity Sensor Utilizing an Electromagnetically Actuated Oscillating Sphere", Conference Paper, pp. 1534-1537, Oct. 28-31, 2011 IEEE.

* cited by examiner

ELECTROMAGNETIC VISCOSITY SENSOR

CROSS REFERENCE TO RELATED APPLICATIONS

This application claims the benefit of an earlier filing date from U.S. Provisional Application Ser. No. 61/451,342 filed Mar. 10, 2011, the entire disclosure of which is incorporated herein by reference.

BACKGROUND

1. Field of the Invention

The present invention relates to the field of downhole fluid analysis in boreholes penetrating the earth. More particularly, the present invention relates to a method and apparatus for estimating fluid density, viscosity, and other parameters using a flexural mechanical resonator downhole in a borehole during monitoring while drilling or wire line operations.

2. Description of the Related Art

There is considerable interest in obtaining density and viscosity for formation fluids downhole at reservoir conditions of extreme temperature and pressure during formation sampling, production, or drilling.

One type of instrument for measuring the density and viscosity of a formation fluid is a flexural mechanical resonator such as a tuning fork. The tuning fork is immersed in a fluid downhole and electrically excited at multiple frequencies. The interaction of the tuning fork with the fluid will introduce additional complex electrical impedance that can be measured in an electrical circuit. It has been shown that this complex electrical impedance can be represented by the sum of two terms: one that is proportional to liquid density and a second one that is proportional to the square root of the viscosity density product.

Unfortunately, conventional flexural mechanical resonators when used downhole can present several problems. For example, a tuning fork may be prone to breakage if not properly protected. Surface contamination of a flexural mechanical resonator due to being disposed downhole may cause low repeatability in resonator measurements. Flexural mechanical resonators, which use permanent magnets, may be prone to attract magnetic particles. These magnetic particles cannot be removed downhole and can affect the accuracy of measurements.

It is important for flexural mechanical resonators to function properly downhole because it can be very expensive in time and equipment if they fail and have to be extracted from the borehole, repaired or replaced, and then sent back down the borehole. It would be well received in the drilling industry if flexural mechanical resonators could be made more robust to survive the extreme environment downhole.

BRIEF SUMMARY

Disclosed is an apparatus for estimating a property of a downhole fluid. The apparatus includes: a flexural mechanical resonator having at least one magnetic permeable element traversing a pressure-retaining wall with a portion of the magnetic permeable element protruding into the fluid, the portion of the magnetic permeable element protruding into the fluid being configured to oscillate; and a monitor for receiving a response of the flexural mechanical resonator to estimate the property.

Also disclosed is a method for estimating a property of a downhole fluid. The method includes: disposing a flexural mechanical resonator in the downhole fluid, the flexural mechanical resonator having at least one magnetic permeable element traversing a pressure-retaining wall with a portion of the magnetic permeable element protruding into the fluid, the portion of the magnetic permeable element protruding into the fluid being configured to oscillate; and receiving a response of the flexural mechanical resonator with a monitor to estimate the property.

Further disclosed is an apparatus for estimating a property of a downhole fluid. The apparatus includes: a sample chamber configured to contain a sample of the downhole fluid for retrieval from downhole; a pump configured to pump the sample of the downhole fluid into the sample chamber; a flexural mechanical resonator having at least one magnetic permeable element traversing a pressure-retaining wall with a portion of the magnetic permeable element protruding into the sample, the portion of the magnetic permeable element protruding into the sample being configured to oscillate; and a monitor for receiving a response of the flexural mechanical resonator to estimate the property.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Figure 1:
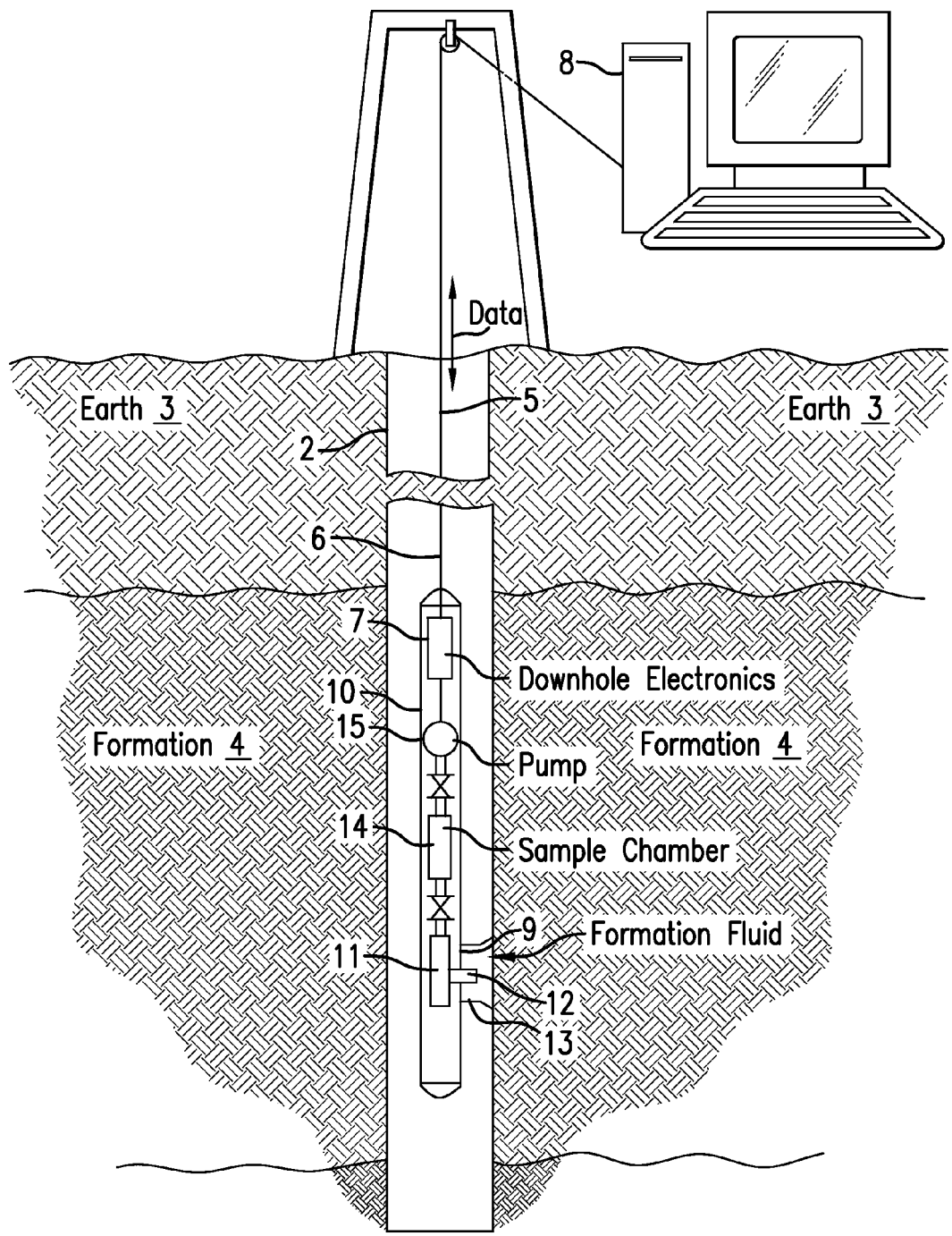
FIG. 1 illustrates an exemplary embodiment of a downhole tool disposed in a borehole penetrating the earth.

FIG. 1 illustrates an exemplary embodiment of a downhole tool 10 disposed in a borehole 2 penetrating the earth 3, which includes an earth formation 4. The formation 4 represents any subsurface material of interest such as a formation fluid or a downhole fluid. A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof. The downhole tool 10 is conveyed through the borehole 2 by a carrier 5. In the embodiment of FIG. 1, the carrier 5 is an armored wireline 6. Besides supporting the downhole tool 10 in the borehole 2, the wireline 6 can also provide communications between the downhole tool and a computer processing system 8 disposed at the surface of the earth 3. In logging-while-drilling (LWD) or measurement-while-drilling (MWD) embodiments, the carrier 5 can be a drill string. In order to operate the downhole tool 10 and/or provide a communications interface with the surface computer processing system 8, the downhole tool 10 includes downhole electronics 7.

Still referring to FIG. 1, the downhole tool 10 includes a flexural mechanical resonator (FMR) 11 for estimating density, viscosity, and/or other parameters of a downhole fluid such as the formation fluid. In one or more embodiments, the FMR 11 is configured to undergo bending or torsional flexing in order to estimate the property of interest. The FMR 11 includes a magnetic element 12 for vibrating or oscillating in the downhole fluid with an oscillation characteristic related to the parameter being measured. In one embodiment, the magnetic element 12 is magnetically excited at a specific frequency fe and an amplitude of vibration is measured. The specific frequency fe and the amplitude of vibration can be measured as a complex electrical impedance in an electrical circuit. In one embodiment, the amplitude of vibration is measured as a result of changes in magnetic coupling as the magnetic element 12 vibrates or oscillates. As previously noted, the complex electrical impedance includes one term that is proportional to liquid density and a second term that is proportional to the square root of the viscosity density product. In addition to frequency and amplitude measurements, dampening of a measured characteristic such as amplitude can also be measured and correlated to a property of the downhole fluid of interest. In one embodiment, amplitude versus frequency is plotted or correlated for several types of fluids beforehand for reference. The measured amplitude and frequency plot is then compared to the reference plots to identify the downhole fluid of interest.

In the embodiment depicted in FIG. 1, the downhole tool 10 includes a formation tester 13 configured to extract a formation fluid from the formation 4 for analysis downhole. A portion of the magnetic element 12 is immersed in the formation fluid at ambient borehole conditions. Another portion of the magnetic element 12 and associated electronics are disposed internal to the downhole tool 10 behind a pressure-retaining wall 9 where conditions are less severe (i.e., lower pressure and/or temperature) than the borehole environment. Alternatively, in another embodiment, a pump 15 pumps a sample of the downhole fluid of interest into a sample chamber 14, which is then retrieved from the borehole 2. Upon retrieval from the borehole 2, the sample can be tested using the FMR 11 either in the sample chamber 14 or after the sample is removed from the sample chamber 15.

Figure 2:
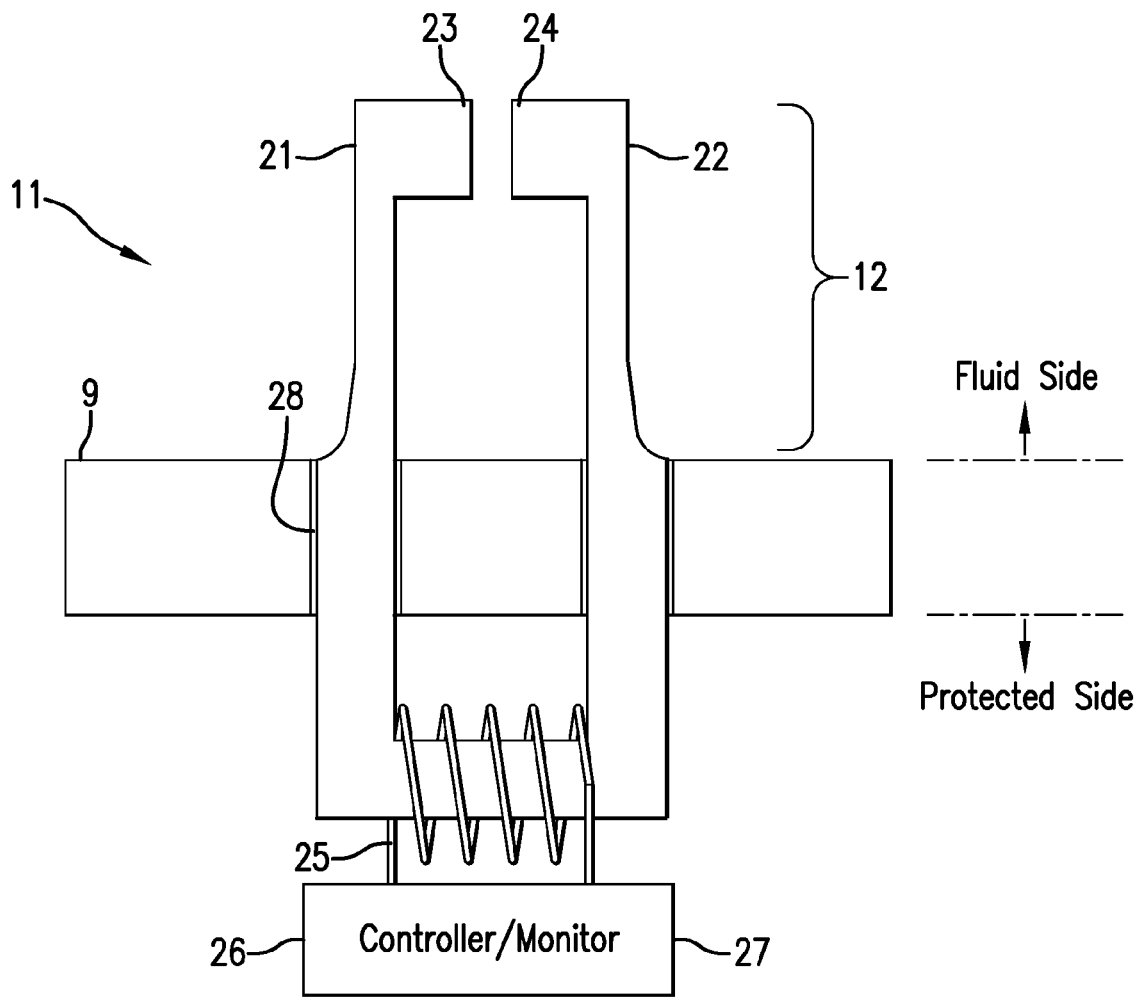
FIG. 2 depicts aspects of a flexural mechanical resonator having resonating magnetic elements.

Reference may now be had to FIG. 2 depicting aspects of an embodiment of the FMR 11. The FMR 11 in FIG. 2 includes a first magnetic element 21 and a second magnetic element 22. The first magnetic element 21 is coupled to the second magnetic element to form one continuous magnetic element on the protected side of the pressure-retaining wall 9. Overall, the magnetic elements 21 and 22 coupled together form a U-shape. A coil 25 surrounds the magnetic elements 21 and 22 on the protected side of the pressure-retaining wall 9. A controller 26 electrically excites the coil 25 at one or more frequencies to actuate the FMR 11. The magnetic elements 21 and 22 are made of a material having a high magnetic permeability such as steel. Hence, when electric current is applied to the coil 25, the magnetic elements are magnetized. The first magnetic permeable element 21 includes a first magnetic pole face 23 and the second magnetic permeable element 22 includes a second magnetic pole face 24. The magnetic pole faces 23 and 24 face each other and have opposite magnetic poles. Thus, when electric current is applied to the coil 25, the magnetic pole faces 23 and 24 attract each other causing the magnetic permeable elements 21 and 22 to bend towards each other. When the electric current flow is stopped or reversed to demagnetize the magnetic permeable elements 21 and 22, the magnetic permeable elements 21 and 22 will spring back to their original positions or to a relaxed position dependent on their magnetization state.

Still referring to FIG. 2, the electric current is applied to the coil 25 at the excitation frequency fe by the controller 26 to cause portions of the magnetic permeable elements 21 and 22 exposed to the fluid of interest to vibrate. The magnetic permeable elements 21 and 22 vibrate with a characteristic related to a parameter of interest being measured. As the magnetic permeable elements 21 and 22 vibrate, the magnetic coupling between the magnetic pole faces 23 and 24 changes, which affects the complex electrical impedance of the coil 25. The complex electrical impedance is measured by a monitor 27. Correlating the complex electrical impedance to the parameter of interest can be accomplished by the monitor 27, the downhole electronics 7, or the surface computer processing system 8. It can be appreciated that the functions of the controller 26 and the monitor 27 can be performed by one electronic unit or distributed among multiple electronic units.

Still referring to FIG. 2, the first magnetic permeable element 21 and the second magnetic permeable element 22 are attached and sealed to the pressure retaining wall 9 using attachment seals 28, which can be an adhesive or solder as non-limiting examples.

Figure 3A:
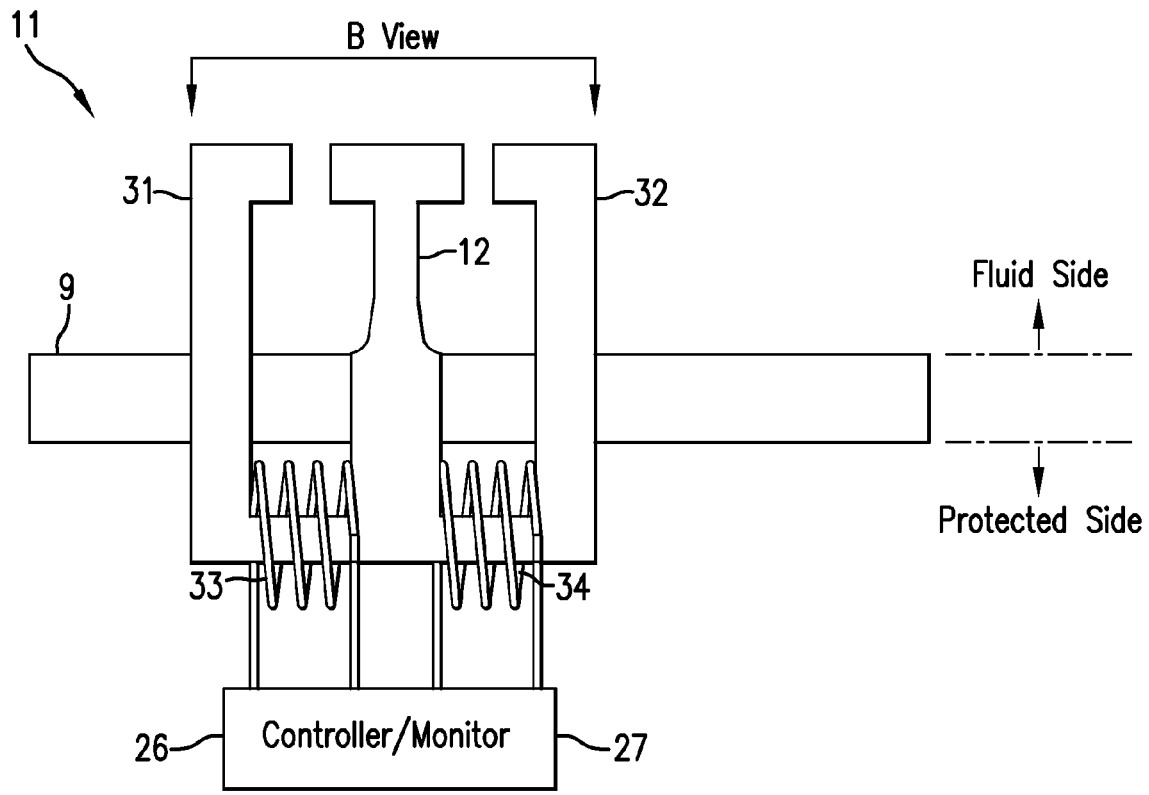
FIGS. 3A and 3B, collectively referred to as FIG. 3, depict aspects of a flexural mechanical resonator having a rotationally resonant magnetic element.
Figure 3B:
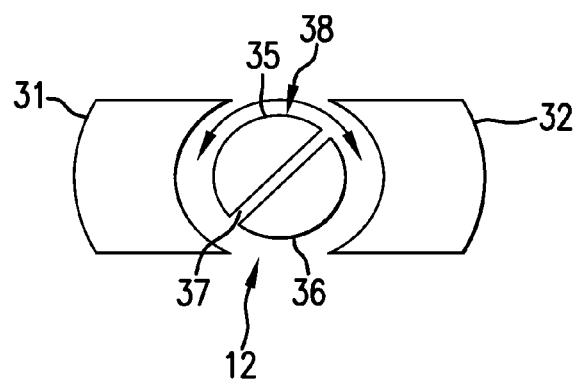

Reference may now be had to FIG. 3 depicting a second embodiment of the FMR 11. In the embodiment of FIG. 3, the magnetic element 12 is configured to rotationally oscillate or vibrate due to a changing magnetic field. The magnetic element 12 includes a first magnetic pole element 35 and a second magnetic pole element 36 separated by a non-magnetic material 37 as shown in FIG. 3B. The magnetic pole elements 35 and 36 can have a texture (or roughness) 38 on an exterior surface configured to improve interaction with the fluid of interest as the magnetic element rotationally oscillates.

In order to apply the changing magnetic field to the magnetic element 12, the FMR 11 includes a first magnetic field source element 31 and a second magnetic field source element 32 as shown in FIGS. 3A and 3B. The first magnetic field source element 31 is magnetically coupled to the first magnetic pole element 35 on the protected side of the pressure-retaining wall 9. Similarly, the second magnetic field source element 32 is magnetically coupled to the second magnetic pole element 36 on the protected side of the pressure-retaining wall 9. A first coil 33 surrounds the first magnetic field source element 31 on the protected side of the pressure-retaining wall 9 and a second coil 34 surrounds the second magnetic field source element 32 also on the protected side of the pressure-retaining wall 9.

The controller 26 and the monitor 27 are coupled to the first coil 33 and the second coil 34. The controller 26 applies an alternating current or current pulses to the first coil 33 to magnetize the first magnetic pole element 35 and the first magnetic field source element 31 thereby applying a torque on the magnetic element 12 and causing the magnetic element 12 to rotate until the applied torque equals a counter-torque from the material of the magnetic element 12. The alternating current or zero current phase of the current pulses will also de-magnetize the elements 35 and 31 to cause the magnetic element 12 to rotationally spring back to its original position. Similarly, the controller 27 will apply an alternating current to the second coil 34 to magnetize and de-magnetize the second magnetic pole element 36 and the second magnetic field source element 32 also urging the magnetic element 12 to rotate and then spring back to its original position. Hence, the magnetic element 12 will rotationally oscillate with a characteristic related to a property of the downhole fluid in which the magnetic element 12 is immersed.

As the magnetic element 12 rotationally oscillates, the magnetic coupling between the first magnetic pole element 35 and the first magnetic field source 31 changes in relation to an amount of rotation of the magnetic element 12. Similarly, the magnetic coupling between the second magnetic pole element 36 and the second magnetic field source 32 changes in relation to an amount of rotation of the magnetic element 12. The magnitude of rotation can be measured by the monitor 27 measuring currents induced in the coils 33 and 34 due to magnetic flux changes in the coils 43 and 44 resulting from the changes in the magnetic coupling with the magnetic element 12.

Figure 4:
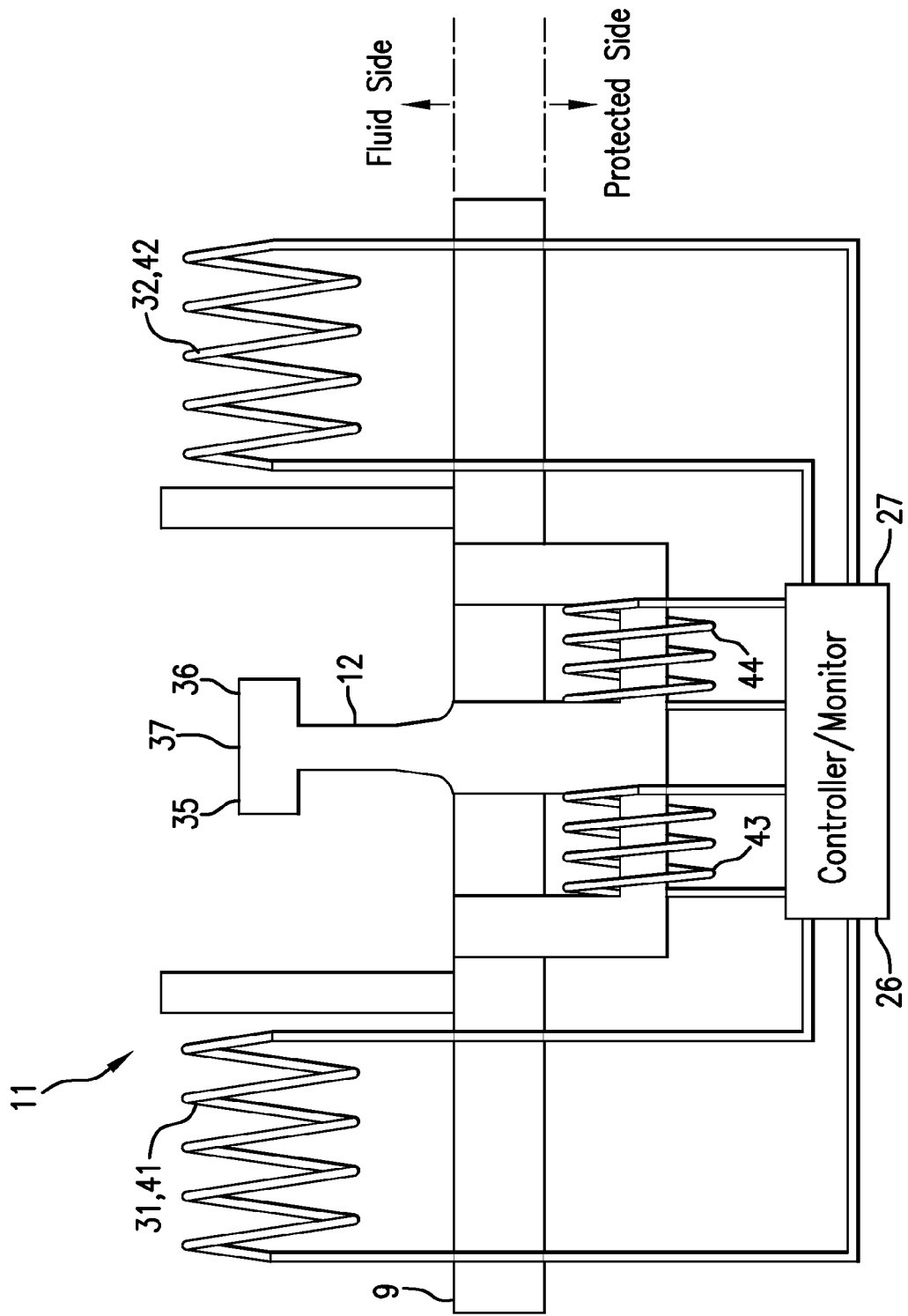
FIG. 4 depicts aspects of another embodiment of a flexural mechanical resonator having external excitation coils immersed in a downhole fluid.

FIG. 4 illustrates a third embodiment of the FMR 11. In the embodiment depicted in FIG. 4, the magnetic element 12 is configured to rotationally oscillate similar to the embodiment of FIG. 3. In FIG. 4, the first magnetic field source element 31 is a coil 41 and the second magnetic field source element 32 is a coil 42. Alternating current or current pulses are applied to the coils 41 and 42 by the controller 26. The first magnetic pole element 35 and the second magnetic pole element 36 are magnetized by coils 43 and 44 respectively. In one embodiment, the controller 26 applies direct current to the coils 43 and 44 to magnetize the magnetic pole elements 35 and 36 respectively. The monitor 27 is coupled to the coils 43 and 44 and measures the magnitude of the rotational oscillations of the magnetic elements 12 as in the embodiment of FIG. 3.

It can be appreciated that the FMR 11 has several substantial advantages over conventional flexural mechanical resonators. One advantage is that the portion of the magnetic permeable element 12 immersed in the downhole fluid can be made as a steel beam to be robust enough to survive the downhole environment. Electronic circuit components such as the controller 26 and the monitor 27 are not immersed in the downhole fluid and are disposed on the protected side of the pressure-retaining wall 9.

Another advantage of the FMR 11 is that magnetic particles will not be permanently attracted to the magnetic permeable element 12 because the magnetic permeable element 12 is not made as a permanent magnet. Because the magnetic element 12 is only temporarily magnetized during a measurement, any magnetic particles that may happen to be attracted to the magnetic element 12 while magnetized will drop away when the magnetic permeable element 12 is de-magnetized.

Another advantage of the FMR 11 is that the FMR 11 does not emit electric fields into the downhole fluid being characterized and, thus, measurements are not sensitive to the conductivity of the downhole fluid.

Another advantage of the FMR 11 is that oscillations of the magnetic element 12 will prevent or limit surface contamination from fluid components that could build up on the magnetic element 12 and causing inaccurate measurements.

Figure 5:
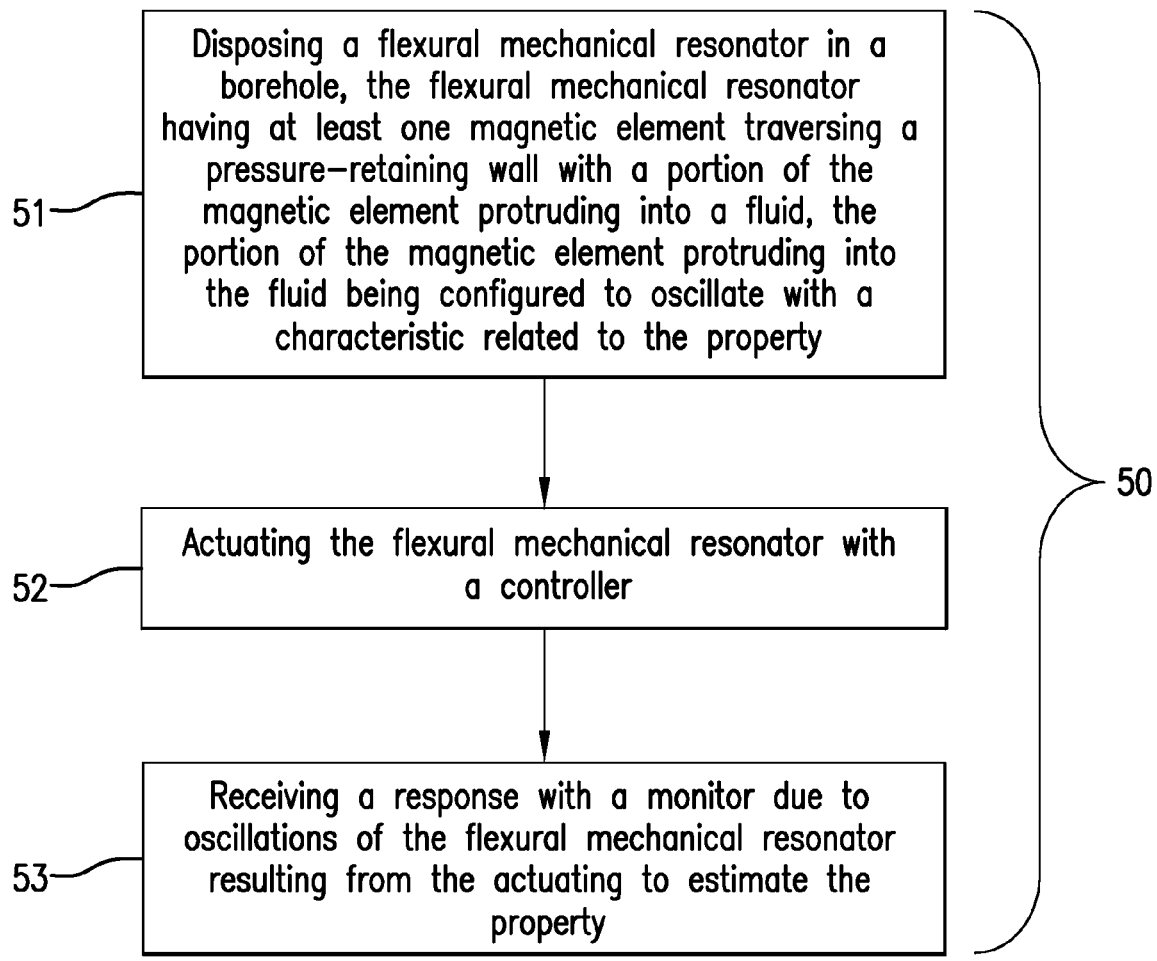
FIG. 5 presents one example of a method for estimating a property of a downhole fluid.

FIG. 5 presents one example of a method 50 for estimating a property of a fluid disposed in a borehole penetrating the earth. The method 50 calls for (step 51) disposing the flexural mechanical resonator 11 in a borehole. Further, the method 50 calls for (step 52) actuating the flexural mechanical resonator 11 with the controller 26. Further, the method 50 calls for (step 53) receiving a response with the monitor 27 due to vibrations or oscillations of the flexural mechanical resonator 11 resulting from the actuating to estimate the property of the fluid. The method 50 can also include pumping a sample of the downhole fluid into the sample chamber 14 using the pump 15. The method 50 can also include retrieving the sample chamber 14 from the borehole and then testing the sample using the FRM 11. The testing can be performed with the sample in the sample chamber or with the sample removed from the sample chamber. The method 50 may also include demagnetizing the flexural mechanical resonator in order to minimize contamination with magnetic particles.

In support of the teachings herein, various analysis components may be used, including a digital and/or an analog system. For example, the downhole electronics 7, the surface computer processing 8, the FMR 11, the controller 26, or the monitor 27 may include the digital and/or analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottomhole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order. The term "couple" relates to two elements being either directly coupled or indirectly coupled via an intermediary element.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating a property of a downhole fluid, the apparatus comprising:
 a flexural mechanical resonator comprising (i) a first magnetic permeable element traversing a pressure-retaining wall with a portion of the first magnetic permeable element protruding into the fluid comprising a first magnetic pole face and (ii) a second magnetic permeable element traversing the pressure-retaining wall with a portion of the second magnetic permeable element protruding into the fluid comprising a second magnetic pole face, the first and second magnetic permeable pole faces being configured to magnetically interact with each other such that the portions of the first and second magnetic permeable elements protruding into the fluid oscillate in resonance with each other; and
 a monitor for receiving a response of the flexural mechanical resonator to estimate the property.

2. The apparatus according to claim 1, wherein the pressure-retaining wall comprises a non-magnetic material.

3. The apparatus according to claim 1, wherein the first magnetic permeable element and the second magnetic permeable element are sealed to the pressure-retaining wall where the first magnetic permeable element and the second magnetic permeable element traverse the pressure-retaining wall.

4. The apparatus according to claim 1, wherein the first magnetic permeable element and the second magnetic permeable element are built from steel.

5. The apparatus according to claim 1, wherein the characteristic is at least one of a frequency, an amplitude, a dampening of a measured characteristic, and a phase shift between measured voltage and current.

6. The apparatus according to claim 1, wherein the property is at least one of density and viscosity.

7. The apparatus according to claim 1, wherein the flexural mechanical resonator is disposed on a carrier configured to be conveyed through the borehole.

8. The apparatus according to claim 1, wherein the carrier comprises a wireline or a drill string.

9. The apparatus according to claim 1, wherein the response is related to oscillations of the flexural mechanical resonator.

10. The apparatus according to claim 1, wherein the first magnetic permeable element is magnetically coupled to the second magnetic permeable element to form a U-shape.

11. The apparatus according to claim 1, further comprising a controller configured for actuating the flexural magnetic resonator.

12. The apparatus according to claim 11, wherein the controller comprises a coil surrounding the at least one magnetic permeable element on a side of the pressure-retaining wall not exposed to the fluid.

13. An apparatus for estimating a property of a downhole fluid, the apparatus comprising:
 a flexural mechanical resonator comprising at least one magnetic permeable element traversing a pressure-retaining wall with a portion of the magnetic permeable element protruding into the fluid, the portion of the magnetic permeable element protruding into the fluid being configured to oscillate; and
 a monitor for receiving a response of the flexural mechanical resonator to estimate the property;
 wherein the at least one magnetic permeable element comprises a first magnetic permeable pole and a second magnetic permeable pole, the magnetic permeable poles being configured to rotationally oscillate the at least one magnetic permeable element.

14. The apparatus according to claim 13, further comprising a non-magnetic wall separating the first magnetic pole from the second magnetic pole.

15. The apparatus according to claim 14, wherein the first magnetic field source element comprises a first coil coupled to the controller and disposed adjacent to the first magnetic permeable pole on a side of the pressure-retaining wall exposed to the fluid and the second magnetic field source element comprises a second coil coupled to the controller and disposed adjacent to the second magnetic permeable pole on a side of the pressure-retaining wall exposed to the fluid.

16. The apparatus according to claim 13, further comprising a first magnetic field source element and a second magnetic field source element coupled to a controller configured for actuating the at least one magnetic permeable element wherein the first magnetic field source element is disposed adjacent to the first magnetic permeable pole and configured to magnetically interact with the first magnetic permeable pole and the second magnetic field source element is disposed adjacent to the second magnetic permeable pole and configured to magnetically interact with the second magnetic permeable pole such that the magnetic interactions with the first and second magnetic permeable poles cause the at least one magnetic permeable element to rotationally oscillate.

17. The apparatus according to claim 16, wherein each of the first and second magnetic field source elements comprises a magnetic permeable material coupled to the at least one magnetic permeable element on a side of the pressure-retaining wall not exposed to the fluid.

18. The apparatus according to claim 17, further comprising a first coil surrounding the first magnetic field source element on the side of the pressure-retaining wall not exposed to the fluid and a second coil surrounding the second magnetic field source element on the side of the pressure-retaining wall not exposed to the fluid, each of the coils being coupled to the controller.

19. A method for estimating a property of a downhole fluid, the method comprising:
 disposing a flexural mechanical resonator in the downhole fluid, the flexural mechanical resonator comprising (i) a first magnetic permeable element traversing a pressure-retaining wall with a portion of the first magnetic permeable element protruding into the fluid and (ii) a second magnetic permeable element traversing the pressure-retaining wall with a portion of the second magnetic permeable element protruding into the fluid, the portions of the first and second magnetic permeable elements protruding into the fluid being configured to oscillate by magnetically interacting with each other;
 actuating the flexural mechanical resonator by magnetizing the first and second magnetic permeable elements using a coil magnetically coupled to the first and second magnetic permeable elements on a side of the pressure-retaining wall not exposed to the fluid causing the first and second magnetic permeable elements protruding into the fluid to oscillate; and receiving a response of the flexural mechanical resonator with a monitor to estimate the property.

20. The method according to claim 19, further comprising demagnetizing the flexural mechanical resonator in order to minimize contamination with magnetic particles.

21. The method according to claim 19, further comprising actuating the flexural mechanical resonator at a plurality of frequencies.

22. The method according to claim 21, wherein the response comprises an amplitude at each of the frequencies in the plurality.

23. An apparatus for estimating a property of a downhole fluid, the apparatus comprising:
- a sample chamber configured to contain a sample of the downhole fluid for retrieval from downhole;
- a pump configured to pump the sample of the downhole fluid into the sample chamber;
- a flexural mechanical resonator comprising (i) a first magnetic permeable element traversing a pressure-retaining wall with a portion of the first magnetic permeable element protruding into the sample comprising a first magnetic pole face and (ii) a second magnetic permeable element traversing the pressure-retaining wall with a portions of the second magnetic permeable element protruding into the sample comprising a second magnetic pole face, the first and second magnetic permeable pole faces being configured to magnetically interact with each other such that the portions of the first and second magnetic permeable element protruding into the sample being oscillate in resonance with each other; and
- a monitor for receiving a response of the flexural mechanical resonator to estimate the property.

* * * * *